United States Patent
Cho

(10) Patent No.: US 7,219,374 B2
(45) Date of Patent: May 22, 2007

(54) VISOR

(75) Inventor: Byoung-Woo Cho, Yongin (KR)

(73) Assignee: Yupoong, Inc., Seoul (KR)

( * ) Notice: Subject to any disclaimer, the term of this patent is extended or adjusted under 35 U.S.C. 154(b) by 187 days.

(21) Appl. No.: 10/470,057

(22) PCT Filed: Mar. 28, 2002

(86) PCT No.: PCT/KR02/00549

§ 371 (c)(1),
(2), (4) Date: Jul. 24, 2003

(87) PCT Pub. No.: WO03/070038

PCT Pub. Date: Aug. 28, 2003

(65) Prior Publication Data

US 2004/0093655 A1 May 20, 2004

(30) Foreign Application Priority Data

Feb. 19, 2002 (KR) .................................. 2002-8825

(51) Int. Cl.
*A42C 5/02* (2006.01)
(52) U.S. Cl. .......................................................... 2/181
(58) Field of Classification Search .............. 2/12, 2/181, 209.13, 195.1–195.4, 10, 425, DIG. 11, 2/338, 181.2
See application file for complete search history.

(56) References Cited

U.S. PATENT DOCUMENTS

| | | | | | |
|---|---|---|---|---|---|
| 1,921,271 | A | * | 8/1933 | Lubin | 66/170 |
| 2,021,940 | A | * | 11/1935 | Lathrop | 2/321 |
| 4,258,437 | A | * | 3/1981 | Sawatsky | 2/12 |
| 5,442,817 | A | * | 8/1995 | Miner | 2/195.1 |
| 5,519,892 | A | * | 5/1996 | Pizzacar | 2/195.2 |
| 5,704,070 | A | | 1/1998 | Stogner | |
| 5,903,921 | A | * | 5/1999 | Dow | 2/12 |
| 5,918,316 | A | | 7/1999 | Nathamson | |
| 6,006,362 | A | * | 12/1999 | Walsh | 2/209.13 |
| 6,279,168 | B1 | * | 8/2001 | Bean | 2/209.13 |
| 6,282,725 | B1 | * | 9/2001 | Vanidestine, Jr. | 2/421 |
| 6,336,224 | B1 | * | 1/2002 | Wang | 2/195.3 |
| 6,499,144 | B1 | * | 12/2002 | Yan | 2/181.2 |
| 2004/0199979 | A1 | * | 10/2004 | Ngan | 2/195.1 |
| 2004/0250336 | A1 | * | 12/2004 | Cho | 2/171 |

FOREIGN PATENT DOCUMENTS

| | | |
|---|---|---|
| CN | 2295348 Y | 10/1998 |
| CN | 1379628 A | 11/2002 |
| JP | 98-25615 | 1/1998 |
| KR | 01-246436 | 8/2001 |
| WO | WO 99/55182 | 11/1999 |
| WO | 03/070038 A1 | 8/2003 |

* cited by examiner

OTHER PUBLICATIONS

The Third Office Action issued by the State Intellectual Property Office of People's Republic of China on Jun. 17, 2005 in Application No. 02804057.0 (5 pages).

*Primary Examiner*—Katherine Moran
(74) *Attorney, Agent, or Firm*—Staas & Halsey LLP

(57) ABSTRACT

A visor assembly includes a visor portion for blocking sunlight, a front portion coupled to the visor portion, a first elastic band coupled to both sides of the front portion to encircle a head, and second elastic bands coupled to a portion of the first elastic band. The second elastic bands have elasticity different from that of the first elastic band. As the elasticity of the first elastic band is different from that of the second elastic bands, the bands exerts resultant elasticity that allows the band to stretch for various head sizes and the contracting force at the overlapping portions of the first and second elastic bands is enhanced, thereby improving the wearing comfort. Furthermore, the first elastic band may be enclosed by a cover in order to satisfy a variety of consumer desires.

23 Claims, 13 Drawing Sheets

VISOR

BACKGROUND OF THE INVENTION (a) Field of the Invention

The present invention relates to a visor, and more particularly, to a visor assembly that is designed to be used regardless of head size and that can provide an advertising effect without affecting its function.

(b) Description of the Related Art

Generally, a visor assembly is used for shading or protecting the face from light. The visor assembly comprises a headband for fixing on the head and a visor portion projecting from the headband to shade and protect the face from sunlight. The headband is generally formed of elastic material so that it can be worn regardless of the size of the head. Furthermore, letters, logos, or trademarks may be embroidered on the headband to obtain an advertisement effect.

In the above-described visor assembly, although the elastic headband can be fitted on any size of head, since there is a sharp difference in the head size between children and adults, visors having a different size from each other should be manufactured, resulting in deterioration in productivity and increase in stock. Furthermore, when several users having different head sizes alternately use one visor assembly, the elasticity of the elastic band is deteriorated and then the visor assembly provides the users with uncomfortable wearing.

In addition, the elasticity of the headband is achieved by forming a strip in a wrinkle-shape. This wrinkle-shape causes the user discomfort, as the headband directly contacts the head.

Specifically, when the letters or trademarks for an advertisement are embroidered on the headband, the elasticity of the headband as well as wearing comfort sharply deteriorates.

SUMMARY OF THE INVENTION

Therefore, the present invention has been made in an effort to reduce the above-described problems of the conventional visor assembly.

It is an objective of the present invention to provide a visor assembly that has improved wearing comfort and improved elasticity regardless of the head size of users, for example, from children to adult head sizes.

It is another objective of the present invention to provide an advertising effect by displaying advertising letters and trademarks.

It is another objective of the present invention to provide a visor assembly that can selectively and variably display an advertisement to improve the problems of the conventional cap designed to display only one fixed advertisement.

It is still another objective of the present invention to provide a visor assembly that is provided with a receiving space in which small items can be temporarily deposited, thereby providing convenience to the user.

To achieve the above objectives, the present invention provides a visor assembly comprising a visor portion for blocking sunlight; a front portion coupled to the visor portion; a first elastic band coupled to both sides of the front portion to encircle a head; and second elastic bands coupled to a portion of the first elastic band, the second elastic bands having an elasticity different from that of the first elastic band.

As the elasticity of the first elastic band is different from that of the second elastic bands, the bands exerts resultant elasticity that allows the band to stretch for various head sizes and the contracting force at the overlapping portions of the first and second elastic bands is enhanced, thereby improving wearing comfort. Furthermore, the first elastic band may be enclosed by a cover so that wearing sensation can be varied depending on the quality of the cover, thereby fulfilling the variety of consumer desires.

According to another aspect of the present invention, a cap assembly comprises a visor portion for blocking sunlight; a front portion coupled to the visor portion; an elastic band coupled to the front portion to encircle a head; and a cover enclosing the elastic band.

Since the elastic band is enclosed by a cover, the wearing sensation may be varied depending on the quality of the cover, thereby fulfilling the variety of consumer desires.

Particularly, by embroidering letters or a logo or attaching an advertising member on the cover, the advertising effect can be obtained without affecting the elasticity of the band portion.

DETAILED DESCRIPTION OF THE PREFERRED EMBODIMENTS

Preferred embodiments will be described in more detail in conjunction with accompanying drawings.

Figure 1:
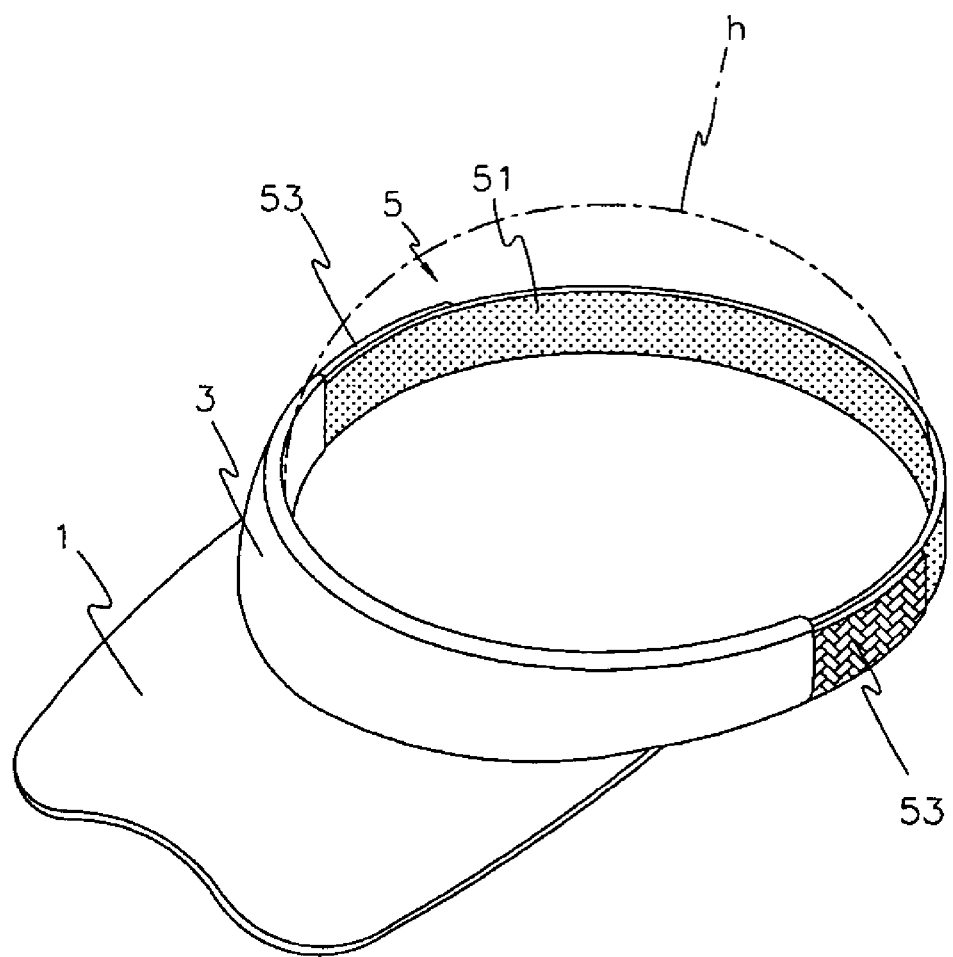
FIG. 1 is a perspective view of a visor assembly according to a first embodiment of the present invention.

FIG. 1 shows a visor assembly according to a first embodiment of the present invention. The inventive visor assembly comprises a visor portion 1, a front portion 3 coupled to one side of the visor portion, and a headband portion 5 connected to both sides of the front portion 3 to encircle the circumference of a head h.

The front portion 3 is coupled to the visor portion 1 by, for example, needlework, and is disposed to preferably shade a forehead.

The headband portion 5 comprises a first elastic band 51 and second elastic bands 53. The first elastic band 51 is formed in an endless circle and is connected to the front portion 3. Each second elastic band 53 is connected at its one end to the front portion 3 and is coupled at its other end to the first elastic band 51.

Preferably, the elasticity of the second elastic bands 53 is less than that of the first elastic band 51.

In the first embodiment of the present invention, the second elastic bands 53 are disposed on an outer side of the first elastic band 51. However, the present invention is not limited to this. That is, the second elastic bands 53 may be coupled to an inner side of the first elastic band 51.

When the headband portion 5 is put on the circumference of a head h of a user, the second elastic bands 53 and parts of the first elastic band 51, which are overlapped with each other, contract against the circumference of the head h. Further, the other part of the first elastic band 51 having a different elasticity also contracts against the circumference, thereby being worn comfortably on the head regardless of the head size from children whose sizes are relatively small to adults whose sizes are relatively large. That is, when the headband portion 51 is put on the head, the first elastic band 51 is expanded, and the second elastic bands 53 having a different elasticity are also expanded, thereby maintaining the comfortable fit.

Figure 2:
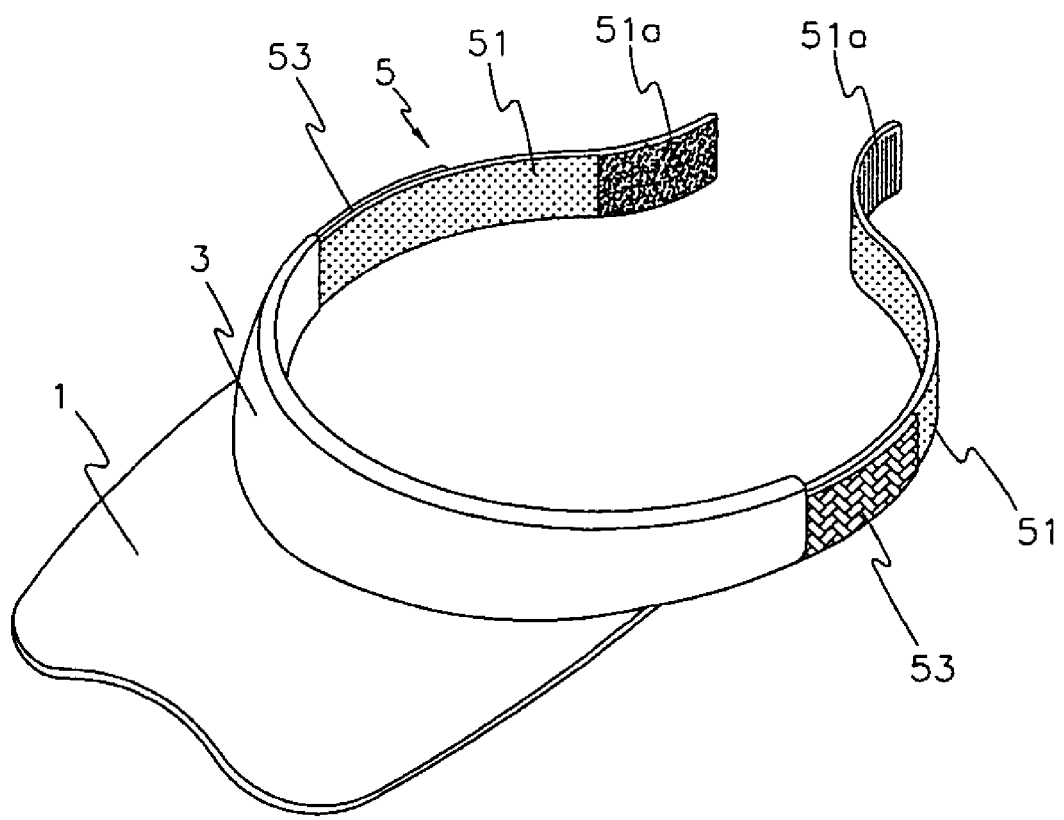
FIG. 2 is a perspective view of a visor assembly according to a second embodiment of the present invention.

Referring to FIG. 2, a visor assembly according to a second embodiment of the present invention will be described. The visor assembly of this embodiment comprises a visor portion 1, a front portion 3 coupled to one side of the visor portion 1, a first elastic band 51 and second elastic bands 53. The first elastic band 51 is divided into two parts. Each part is coupled to a side of the front portion 3 and has a free end. The second elastic bands 53 are coupled to the side of the front portion 3 and are further coupled to a portion of the first elastic band 51. A Velcro fastener 51a is provided on each free end of the first elastic band 51 so that the first elastic band ends can be coupled to each other.

The first elastic band 51 has a different elasticity from that of the second elastic bands 53 as in the first embodiment. Therefore, the operation is similar to that of the first embodiment. Further, since the first elastic band 51 is designed to have its ends coupled by the Velcro fastener 51a in the second embodiment, it can be more effectively used regardless of the head size. Particularly, even when only one size is provided, the visor assembly can be widely used by children and adults, while providing a comfortable fit. The detailed description of the operation of this embodiment is the same as that of the first embodiment, except that in this embodiment the ends of the first elastic band 51 are coupled with each other by the Velcro fastener 51a before the visor assembly is placed on the head.

Figure 3:
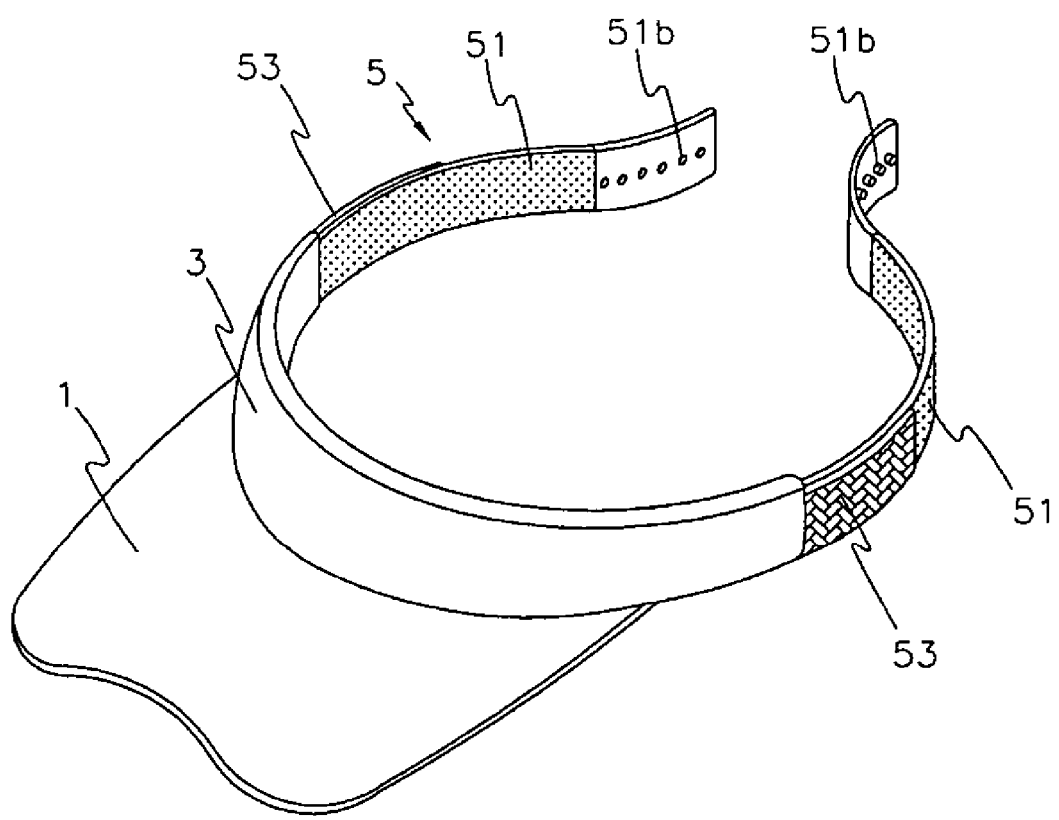
FIG. 3 is a perspective view of a visor assembly according to a third embodiment of the present invention.

FIG. 3 shows a visor assembly according to a third embodiment of the present invention. The visor assembly of this embodiment comprises a visor portion 1, a front portion 3 coupled to the visor portion 1, a first elastic band 51 coupled on both sides of the front portion 3, and second elastic bands 53.

The first elastic band 51 is divided into two parts. Each part is coupled on a side of the front portion 3 and has a free end. The second elastic bands 53 are coupled to the sides of the front portion 3 and are further coupled to a portion of the first elastic band 51. In the third embodiment, the free ends of the first elastic band 51 are provided with connecting hook assembly 51b. The connecting hook assembly 51b has a first portion provided with plural holes disposed at identical distances from each other and a second portion provided with projections for fitting into the holes of the first portion. However, the present invention is not limited to this. That is, any type of connecting structure may be employed. The operation of this embodiment is similar to that of the second embodiment, so the detailed description thereof will be omitted.

Figure 4:
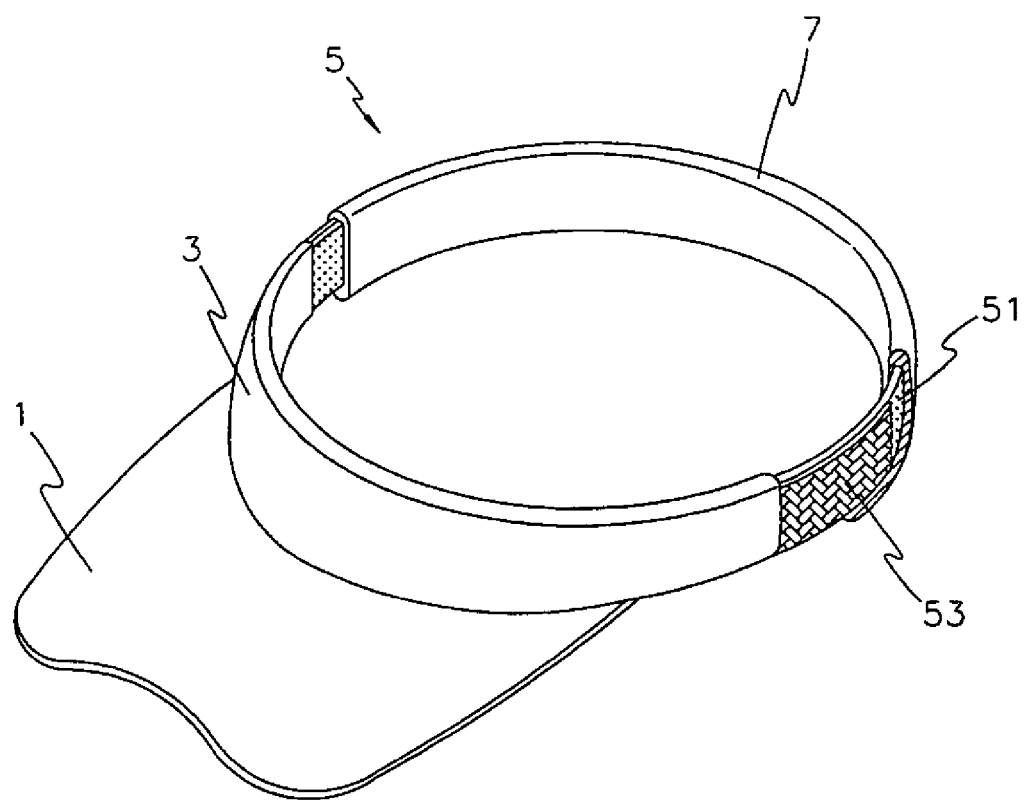
FIG. 4 is a perspective view of a visor assembly according to a fourth embodiment of the present invention.
Figure 5:
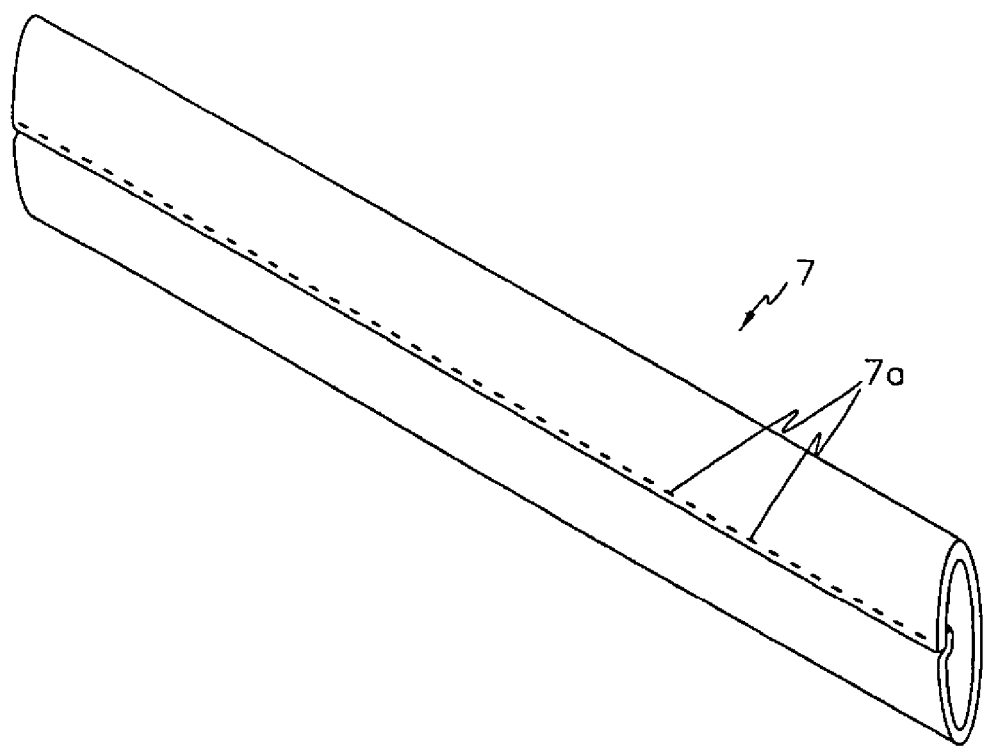
FIG. 5 is a perspective view of a cover depicted in FIG. 4.

Referring now to FIGS. 4-5, a fourth embodiment of the present invention will be described. FIG. 4 shows a visor assembly according to a fourth embodiment of the present invention, and FIG. 5 shows a major part of the fourth embodiment. The visor assembly of this embodiment comprises a visor portion 1, a front portion 3 coupled to the visor portion 1, a headband portion 5 coupled to a side of the front portion 3, and a cover 7 enclosing the outer circumference of the headband portion 5. The headband portion 5 can be as described in the first, second, or third embodiments, and the structure thereof is also similar to those of the embodiments.

The cover 7 prevents the headband portion 5 from directly contacting the head, thereby improving wearing comfort. The cover 7 is preferably formed of soft cloth. Particularly, when the cover portion 7 is formed of a variety of colors or designs, the esthetic appearance thereof may be improved.

FIG. 5 shows a cover employed in the fourth embodiment in more detail. The cover 7 has a space in which the headband portion 5 is inserted, and an overlap portion which is coupled by needlework, thereby forming a needlework-coupling portion 7a.

When the cover 7 is applied to a visor assembly such as the first or fourth embodiment, the headband portion 5 is first inserted into the cover 7 and is then coupled to the front portion 3. The cover is also applied to a visor assembly such as the second or third embodiment. Since the first elastic band 51 is divided, it is easy to couple the first elastic band 51 to the cover. In this case, various kinds of covers may alternately be used. That is, the cover may be changed according to personal taste. Since the headband portion 5 of this embodiment is similar to those of the first, second, and third embodiments, the detailed description thereof will be omitted.

Figure 6:
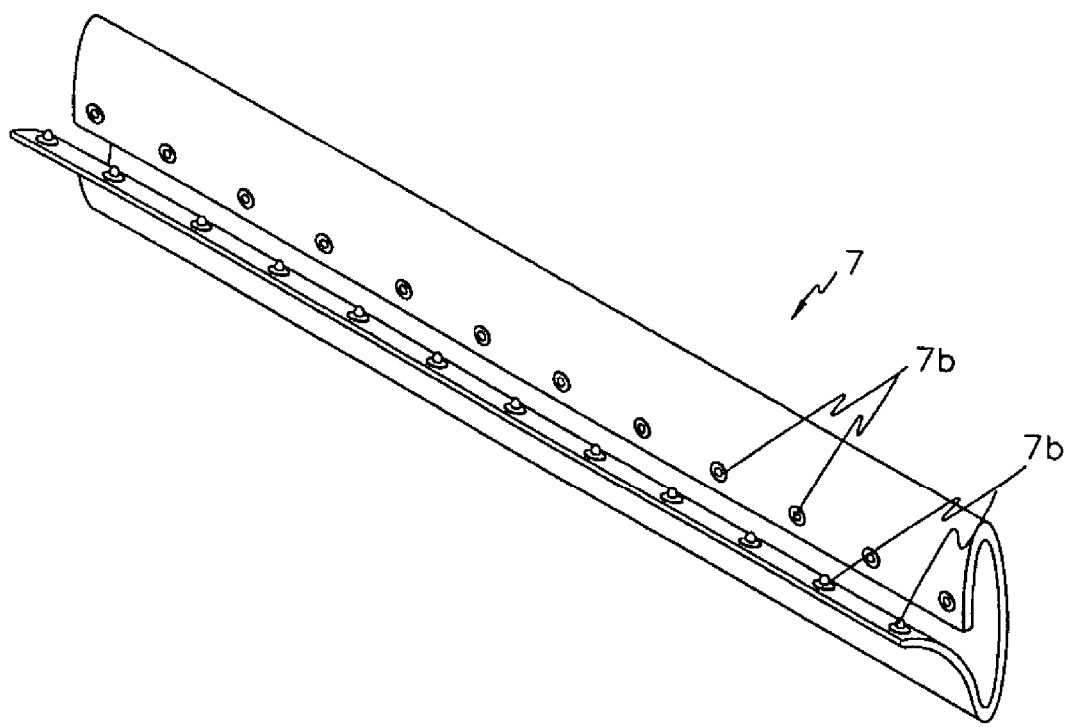
FIG. 6 is a perspective view of a cover depicted in FIG. 4 according to a fifth embodiment of the present invention.

FIG. 6 illustrates another example of a cover 7 in a visor assembly according to a fifth embodiment of the present invention. In this embodiment, since the cover is to enclose the band 5, a plurality of male and female coupling fasteners 7b are provided on the cover 7. Each male and female coupling fastener is coupled. That is, a plurality of holes or grooves are formed on one portion of the male and female coupling fastener 7b, and a plurality of projections to be press-fitted in the holes or grooves are provided on the other side of the male and female coupling fastener 7b. This fifth embodiment is similar to the fourth embodiment, and it is also applied to the headband portion 5 of the fourth embodiment, which is formed in an endless circle. Therefore, this embodiment is capable of various applications.

Figure 7:
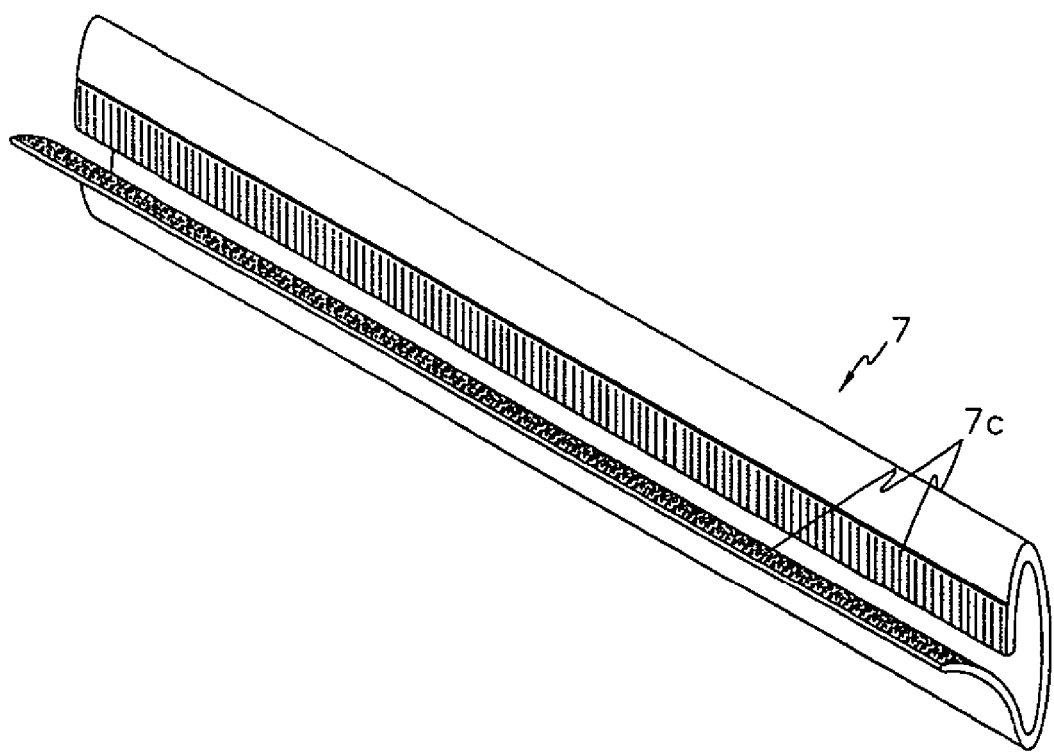
FIG. 7 is a perspective view of a cover depicted in FIG. 4 according to a sixth embodiment of the present invention.

FIG. 7 illustrates still another example of a cover 7 in a visor assembly according to a sixth embodiment of the present invention. This sixth embodiment is similar to the fifth embodiment except that a Velcro fastener 7c instead of the male and female coupling fastener 7b is formed on the overlapping portions of the cover to enclose the band portion 5. The Velcro fastener can increase the application of the present invention in a variety of designs.

Figure 8:
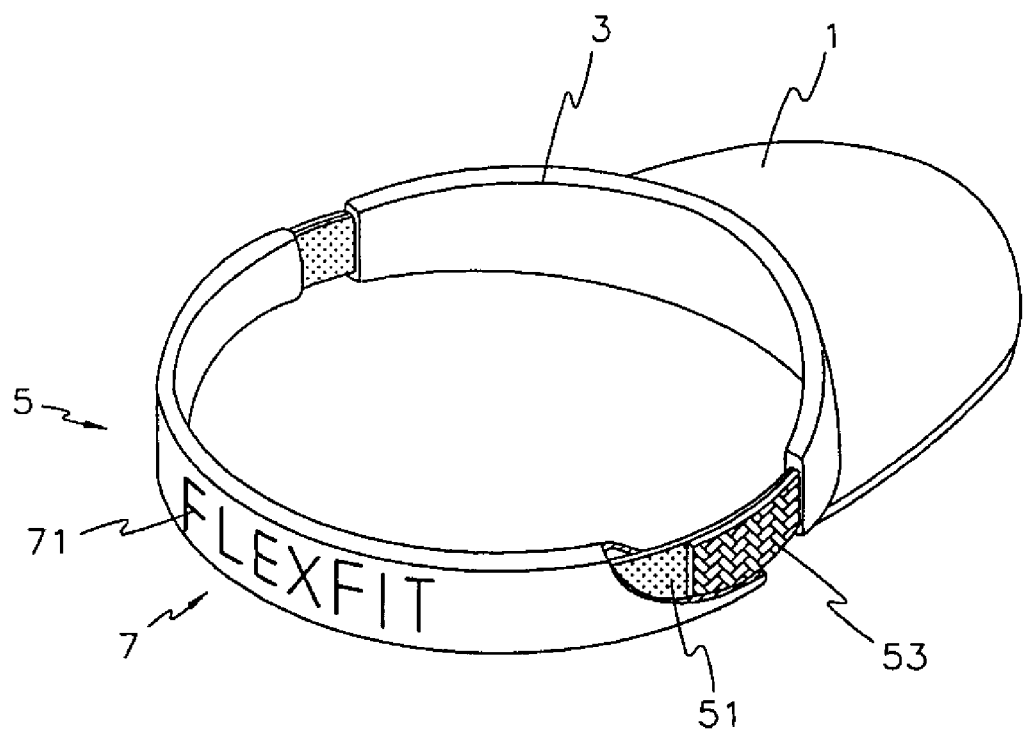
FIG. 8 is a rear view of a modified example of the sixth embodiment of FIG. 7, in which a cover is provided with an advertisement according to a seventh embodiment of the present invention.

Referring to FIG. 8, which shows a perspective view of a visor assembly, a seventh embodiment of the present invention will be described.

In this embodiment, the cover 7 is provided with an advertising portion 71 such as letters or a logo that are embroidered. As the advertising portion 71 is formed on the cover 7, the advertising effect can be obtained without affecting the elasticity of the band portion 5. In this embodiment, when the cover is formed of a high quality colored cloth, the wearing comfort can be further improved while enhancing the advertising effect by the improved esthetic appearance.

Figure 9:
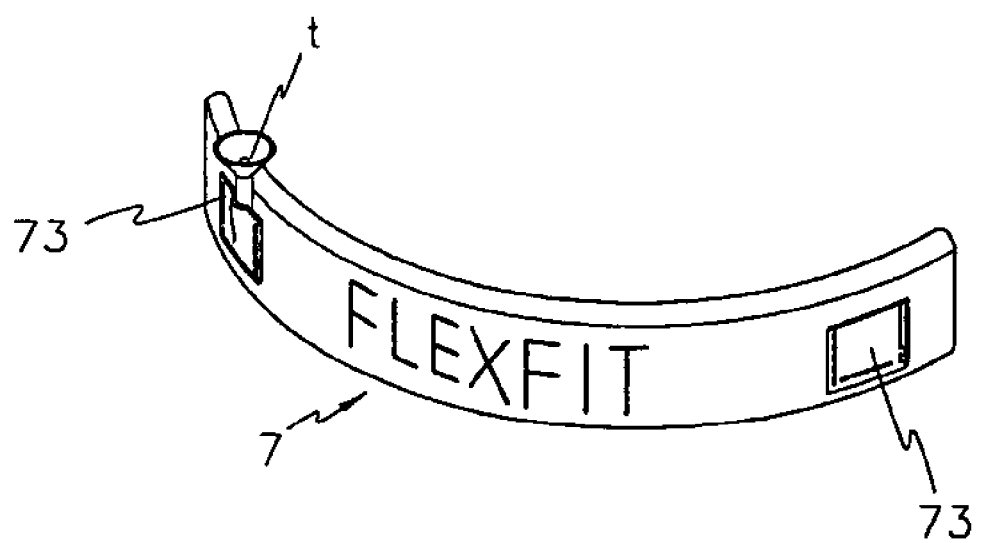
FIG. 9 is a rear view of a modified example of the sixth embodiment of FIG. 7, in which a cover is provided with a receiving pocket according to an eight embodiment of the present invention.

FIG. 9 shows a visor assembly according to an eighth embodiment of the present invention. In this embodiment, the cover 7 is provided with a receiving pocket 73. The receiving pocket 73 is formed to receive small items such as golf tees t. Such a pocket 73 provides the user with convenience without affecting the elasticity of the band portion 5.

Figure 10:
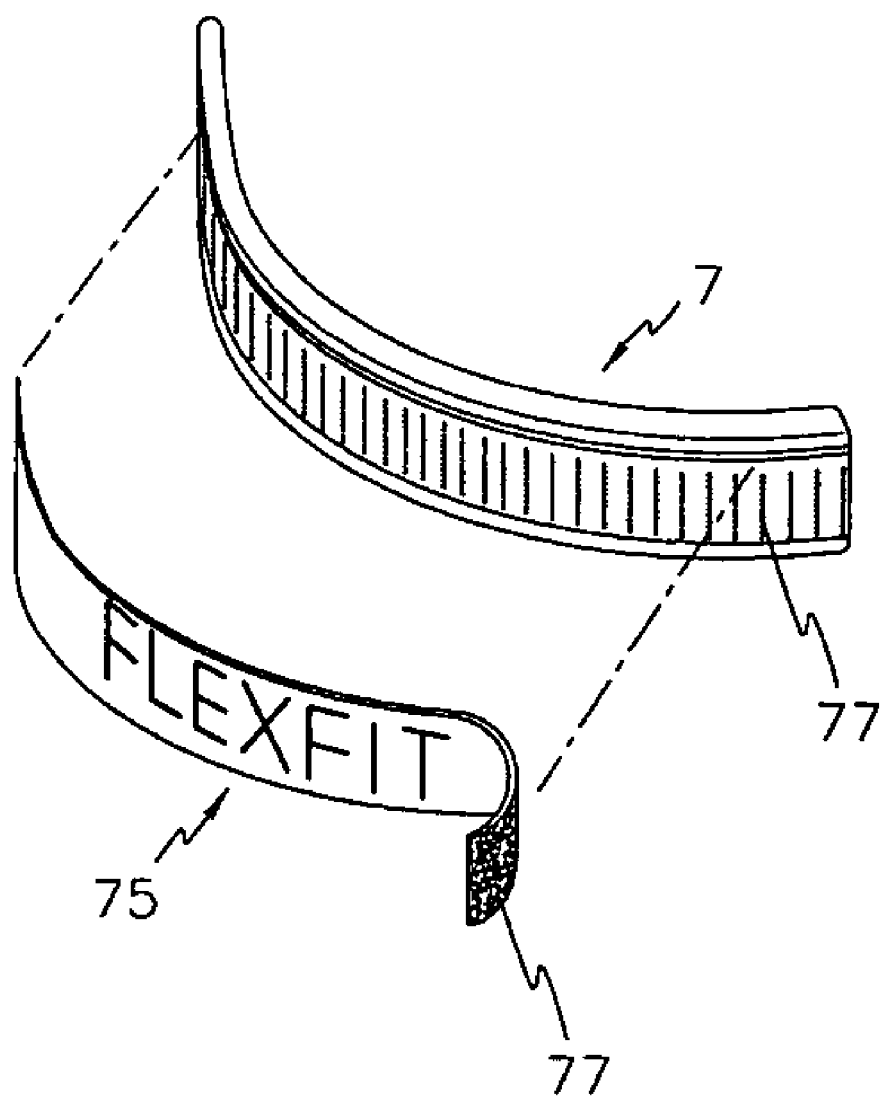
FIG. 10 is a perspective view of a visor assembly according to a ninth embodiment of the present invention.

FIG. 10 shows a visor assembly according to a ninth embodiment of the present invention. In this embodiment, an advertising member 75 is attached to the cover 7. In addition to the letters or logo, a variety of designs may be formed on the advertising member 75 to enhance the esthetic appearance. In this embodiment, such an advertising member 75 is coupled to the cover 7 by a Velcro fastener 77. However, the present invention is not limited to this example, as it is possible to use various fasteners that are capable of detachably attaching the member. The visor assembly of the ninth embodiment has an improved advertising effect over the seventh embodiment as described above, as well as an increased ease of replacing the advertising members with different advertisements at a reduced cost. By detachably attaching the advertising member, a variety of advertising images can be realized alternately without affecting the elasticity of the headband portion 5.

Figure 11:
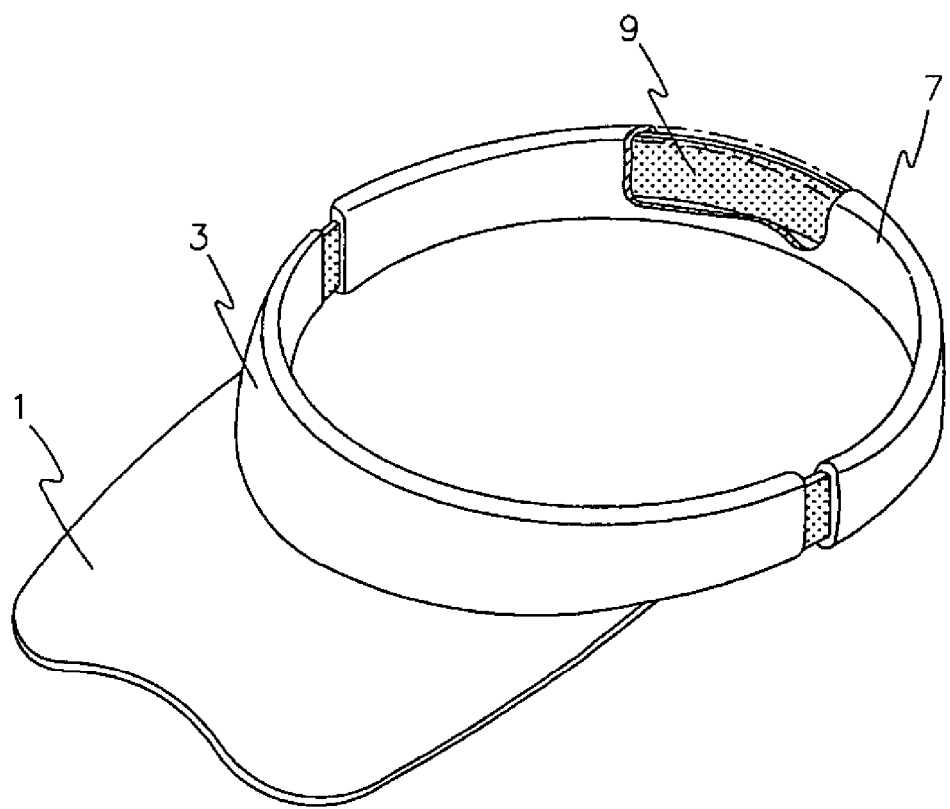
FIG. 11 is a perspective view of a visor assembly according to a tenth embodiment of the present invention.

FIG. 11 shows a visor assembly according to a tenth embodiment of the present invention. A visor assembly of this embodiment comprises a visor portion 1, a front portion 3 coupled to the visor portion 1, an elastic band 9 coupled on both sides of the front portion 3, and a cover 7 disposed on the outer circumference of the elastic band 9.

In the tenth embodiment, the elasticity of the elastic band 9 is uniform. The coupling structure of the elastic band 9 and the cover 7 is similar to those of the above embodiments. That is, this embodiment shows that the cover 7 can be applied to a variety of structures, making it possible to produce a variety of visor assemblies.

Figure 12:
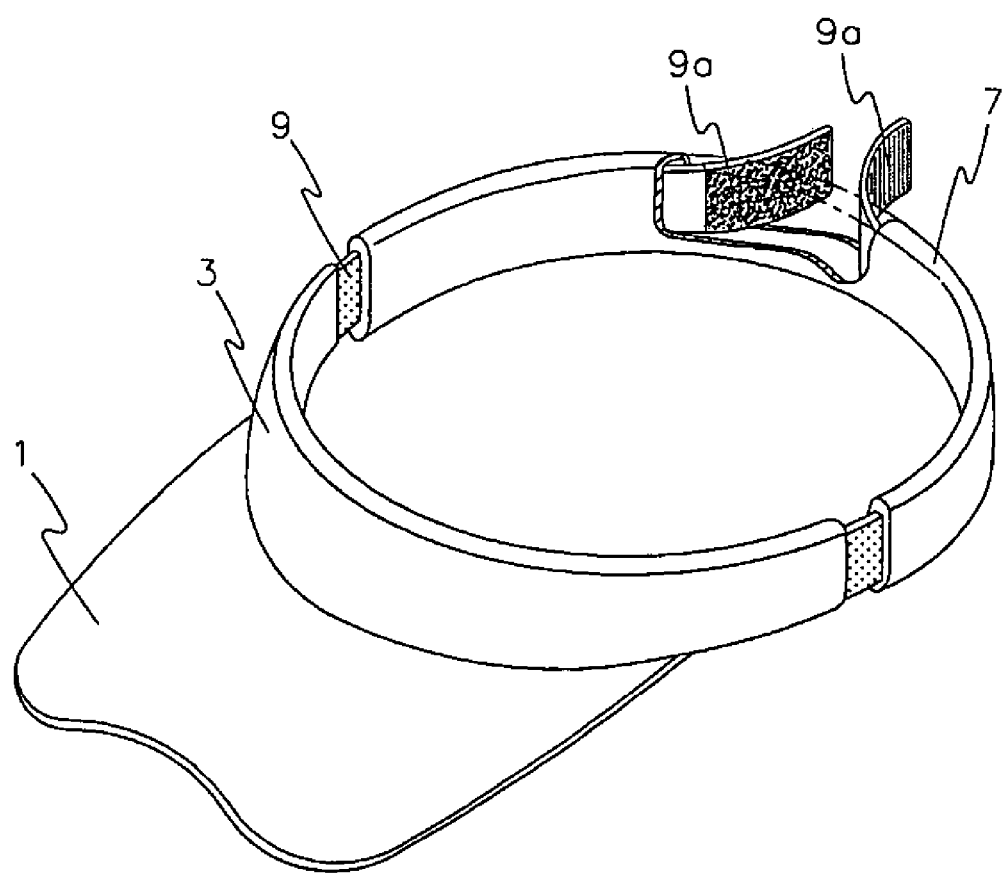
FIG. 12 is a perspective view of a visor assembly according to an eleventh embodiment of the present invention.

FIG. 12 shows a visor assembly according to an eleventh embodiment of the present invention. A visor assembly of this embodiment comprises a visor portion 1, a front portion 3 coupled to the visor portion 1, an elastic band 9 coupled to the front portion 3, and a cover 7 enclosing the elastic band 9.

In this embodiment, the elasticity of the elastic band 9 is uniform. The elastic band 9 is provided with free ends coupled to each other by a Velcro fastener 9a.

It is possible that the elastic band 9 having uniform elasticity is easily coupled with the cover 7 in this embodiment. This embodiment also shows that the cover 7 can be applied in a variety of shapes, making it possible to produce a variety of visor assemblies.

Figure 13:
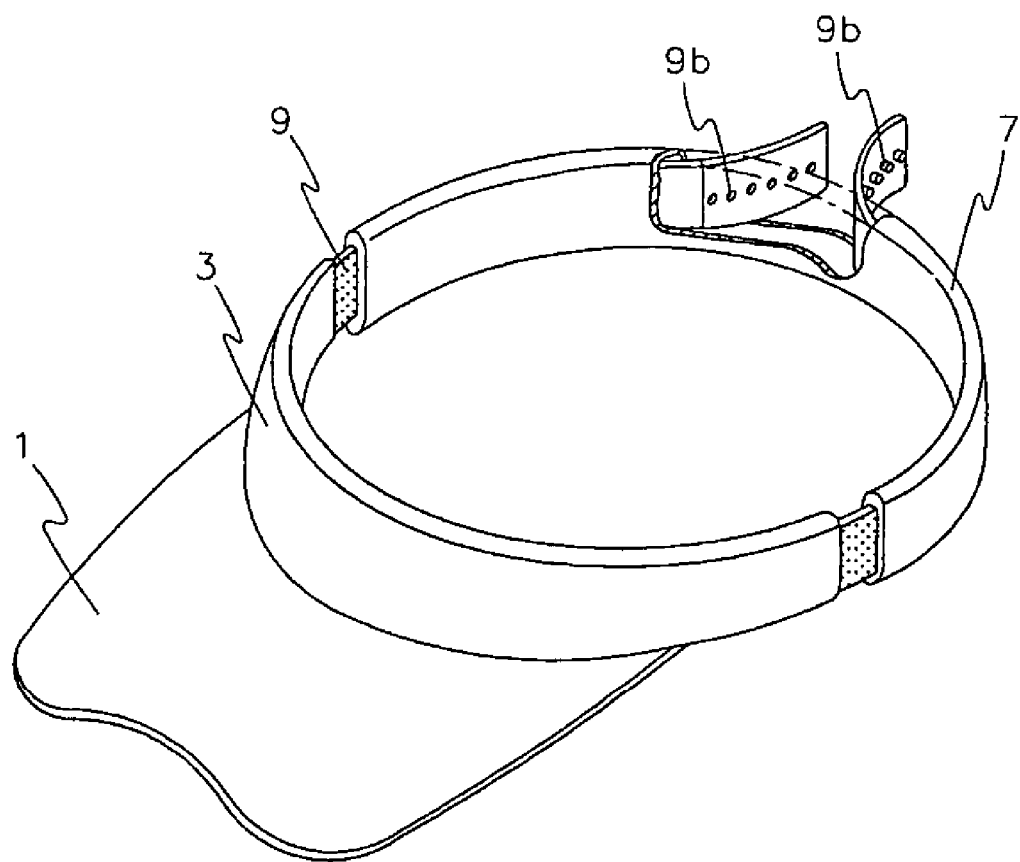
FIG. 13 is a perspective view of a visor assembly according to a twelfth embodiment of the present invention.

FIG. 13 shows a visor assembly according to a twelfth embodiment of the present invention. A visor assembly of this embodiment comprises a visor portion 1, a front portion 3 coupled to the visor portion 1, an elastic band 9 coupled to the front portion 3, and a cover 7 enclosing the elastic band 9. This embodiment is similar to the eleventh embodiment except that the elastic band 9 is detachably attached by male and female fasteners 9b. This shows that the visor assembly of the present invention can have various designs.

As described above, the first and second elastic bands of the first embodiment to the fourth embodiment, whose elasticity is different from each other, are designed to partly overlap each other to maintain the elasticity of the headband portion, thereby providing wearing comfort regardless of head size of the wearer. Furthermore, since a cover is provided to enclose the headband portion, wearing comfort can be further improved.

Particularly, by embroidering letters or logos or by attaching an advertising member on the cover, the advertising effect can be obtained without affecting the elasticity of the headband portion.

In addition, since the cover is provided with a receiving pocket, small items can be conveniently received therein.

Furthermore, since the length of the elastic band can be adjusted by adjusting the Velcro fastener or the connecting hook assembly, the visor assembly can be more effectively applied to a variety of head sizes.

It will be apparent to those skilled in the art that various modifications and variations can be made to the device of the present invention without departing from the scope of the invention. The present invention covers the modifications and variations of this invention provided they come within the scope of the appended claims and their equivalents.

What is claimed is:

1. A visor assembly comprising:
   a visor portion for blocking sunlight;
   a front portion coupled to the visor portion;
   a first elastic band coupled to both sides of the front portion to encircle a head;
   second elastic bands coupled to a portion of the first elastic band, the second elastic bands having an elasticity that is different from that of the first elastic band; and
   a cover enclosing the first elastic band,
   wherein the cover has elasticity.

2. A visor assembly of claim 1, wherein the elasticity of the second elastic bands is less than that of the first elastic band.

3. A visor assembly of claim 1, wherein the cover is formed of cloth.

4. A visor assembly of claim 1, wherein the cover has free ends that are attached to each other by needlework.

5. A visor assembly of claim 1, wherein the cover has free ends that are attached to each other by a plurality of male and female coupling fasteners.

6. A visor assembly of claim 1, wherein the cover has free ends that are attached to each other by a hook and loop fastener.

7. A visor assembly of claim 1, wherein the cover is provided with an advertising portion formed by embroidered letters or a logo.

8. A visor assembly of claim 1, wherein the cover is provided with a receiving pocket.

9. A visor assembly of claim 1, wherein an advertising member is detachably attached to the cover.

10. A visor assembly of claim 9, wherein the cover and the advertising member are attached to each other by a hook and loop fastener.

11. A visor assembly of claim 1, wherein the first elastic band or the elastic band is divided into two sections that are selectively coupled by a hook and loop fastener, thereby making it possible to adjust the length of the first elastic band or the elastic band.

12. A visor assembly of claim 1, wherein the first elastic band or the elastic band is divided into two sections that are selectively coupled by a connecting hook, thereby making it possible to adjust the length of the first elastic band or the elastic band.

13. A method comprising:
coupling a first elastic unit to first and second sides of a front portion of a visor assembly;
coupling second and third elastic units to the first elastic unit and respectively to the first and second sides of the front portion; and
coupling an elastic cover to the first elastic unit,
the first elastic unit having an elasticity different from an elasticity of the second and third elastic units.

14. The method of claim 13, wherein the coupling of the cover comprises inserting the first elastic unit into a space in the cover.

15. The method of claim 13, wherein the coupling of the cover comprises fastening a male portion of the cover with a female portion of the cover.

16. The method of claim 13, wherein the coupling of the cover comprises fastening a hook portion of the cover with a loop portion of the cover.

17. The method of claim 13, further comprising displaying information on the cover.

18. The method of claim 13, further comprising providing a pocket in the cover.

19. The method of claim 13, further comprising attaching a member including information on the cover.

20. The method of claim 13, further comprising coupling the front portion to a visor portion.

21. The method of claim 13, wherein the coupling of the first elastic unit to the first and second sides comprises coupling first and second portions of the first elastic unit respectively to the first and second sides of the front portion.

22. The method of claim 21, further comprising fastening a male portion at a free end of the first portion of the first elastic unit to a female portion at a free end of the second portion of the first elastic unit.

23. The method of claim 21, further comprising fastening a hook portion at a free end of the first portion of the first elastic unit to a loop portion at a free end of the second portion of the first elastic unit.

* * * * *